United States Patent [19]
Portoghese et al.

[11] Patent Number: 5,804,595
[45] Date of Patent: Sep. 8, 1998

[54] KAPPA OPIOID RECEPTOR AGONISTS

[75] Inventors: Philip S. Portoghese, St. Paul, Minn.; An-Chih Chang, Phoenixville, Pa.

[73] Assignee: Regents of the University of Minnesota, Minneapolis, Minn.

[21] Appl. No.: 567,624

[22] Filed: Dec. 5, 1995

[51] Int. Cl.$^6$ .................. A61K 31/135; A61K 31/40; A61K 31/405; C07C 69/616; C07C 237/14; C07D 207/09; C07D 209/12

[52] U.S. Cl. .................. 514/428; 514/429; 514/646; 514/649; 514/414; 514/415; 514/419; 514/422; 548/469; 548/495; 548/517; 548/566; 548/569; 548/571; 548/577; 548/578; 548/579; 548/506; 548/523; 560/39; 560/41; 560/48; 560/51; 562/30; 562/37; 562/44; 562/433; 562/439; 562/440; 562/443; 562/444; 562/455; 564/123; 564/161; 564/182

[58] Field of Search .................. 514/428, 429, 514/646, 649; 548/469, 495, 517, 566, 569, 571, 577, 578, 579, 506, 523

[56] References Cited

U.S. PATENT DOCUMENTS 4,806,556  2/1989  Portoghese .................. 546/44

FOREIGN PATENT DOCUMENTS 0254545  1/1988  European Pat. Off. .
0325406  7/1989  European Pat. Off. .
0374756  6/1990  European Pat. Off. .

OTHER PUBLICATIONS

Chang, A., et al., "k–Opioid Receptor Selective Affinity Labels: Electrophilic Benzeneacetamides as k–selective Opioid Antagonists", *Advance ACS Abstracts*, vol. 2, No. 22, J. Med. Chem., 79–80, (Nov. 15, 1994).

Barber, A., et al., "Opiod Agonists and Antagonists: An Evaluation of Their Peripheral Actions in Inflammation," *Med. Res. Reviews*, 12, 525–562 (1992).

Barlow, J. J., et al., "Structure/Activity Studies Related to 2–(3,4–Dichlorophenyl)–N–methyl–N–[2–(1–pyrrolidinyl)–1–substituted–ethyl]acetamides: A Novel Series of Potent and Selective κ–Opiod Agonists," *J. Med. Chem.*, 34, 3149–3158 (1991).

Birch, P.J., et al., "Preparation and Evaluation of Some Hydrophilic Phenylacetyl–peperazines as Peripherally Selective κ–Opiod Agonists," *Bioorg. Med. Chem. Lett.*, 2, 1275–1278 (1992).

Brown, D. R., et al., "The Use of Quanternary Narcotic Antagonists in Opiate Research," *Neuropharm.*, 24, 181–191 (1985).

Costello, G.F., et al., "2–(3,4–Dichlorophenyl)–N–methyl–N–[2–(1–pyrrolidinyl)–1–substituted–ethyl]acetamides: The Use of Conformational Analysis in the Development of a Novel Series of Opioid κ Agonists," *J. Med. Chem.*, 34, 181–189 (1991).

Martin, W. R., "Pharmacology of Opioids," *Pharmacol. Reviews*, 35, 283–232 (1984).

Rogers, H., et al., "GR94839, a κ–Opioid Agonist with Limited Access to the Central Nervous System, has Antinociceptive Activity," *Br. J. Pharmacol.*, 106, 783–789 (1992).

Shaw, J.S., et al., "ICI 204448: A κ–Opioid Agonist with Limited Access to the CNS," *Br. J. Pharmacol.*, 96, 986–992 (1989).

Simon, E.J., et al., "Opioid Receptor Multiplicity: Isolation, Purification, and Chemical Characterization of Binding Sites," In: *Opioids I*, Herz, A., (ed.), Springer–Verlag, Berlin, pp. 3–26 (1993).

"K Opioid Receptor Selective Affinity Labels: Electrophilic Benzeneacetamides as K–Selective Opioid Antagonists," A. Chang et al., *J. Med. Chem.*(1994) 37, 4490–4498.

*Primary Examiner*—Joseph McKane
*Assistant Examiner*—Jane C. Osweckí
*Attorney, Agent, or Firm*—Schwegman, Lundberg, Woessner & Kluth, P.A.

[57] ABSTRACT

The invention provides certain amino acid conjugates of substituted 2-phenyl-N-[1-(phenyl)-2-(1-heterocycloalkyl- or heterocycloaryl-)ethyl]acetamides useful for selectively agonizing kappa opioid receptors in mammalian tissue.

33 Claims, 4 Drawing Sheets

KAPPA OPIOID RECEPTOR AGONISTS

The present invention was made with the assistance of the National Institute of Health under Grant No. DA08457. The U.S. Government has certain rights in the invention.

BACKGROUND OF THE INVENTION

In spite of its powerful analgesic properties, morphine also induces tolerance, dependence, and respiratory depression. Since the first definitive isolation of morphine in 1805, morphine and other opium-derived molecules have been the subject of a continuous ongoing effort to eliminate the undesirable side-effects while retaining the analgesic properties. Although the elimination of side-effects has not been achieved, structural modifications of morphine and its analogues have led to improved analgesic agents and to the discovery of receptor selective agonists and antagonists which are useful pharmacologic tools. Also, the endogenous opioid peptides have been structurally modified in an effort to develop superior opioid ligands. See, W. R. Martin, Pharmacol. Rev. 35:283 (1984).

Since the first proposal of opioid receptor heterogeneity in 1965, it is now known there are at least three types of opioid receptors, mu ($\mu$), kappa ($\kappa$) and delta ($\delta$) with receptor subtypes in each type (Simon et al., In Opioids I, Herz, Ed. Springer-Verlag: Berlin 3–26 (1993)). Furthermore, pharmacologic studies with receptor selective ligands have shown that analgesia can be produced by selective activation of each of the three types of opioid receptors. In particular, $\kappa$ opioid receptors have attracted special attention because their selective activation can produce analgesia without the dependence and respiratory depression that is associated with $\mu$ receptor activation by morphine.

The $\kappa$ opioid receptors are members of the superfamily of G protein-coupled receptors (GPCRs). Agonist binding to the $\kappa$ receptors activates the intracellularly associated $G_i$ protein, which decreases $Ca^{2+}$ channel conductance or inhibits adenylyl cyclase (AC). In addition to analgesia, potential applications of $\kappa$ selective agonists include the areas of diuresis, eating disorders, motion sickness, and neuroprotection. Therefore, the $\kappa$ receptors represent important therapeutic targets that require extensive studies to allow a better understanding of their mechanisms of action. Ligands selective for the $\kappa$ receptors can serve as important pharmacologic tools in such studies. For example, such compounds can be used in competition assays to determine the relative specificity and selectivity of other compounds for the $\kappa$ receptor, as well as for $\mu$ and $\delta$ receptors.

However, the use of opioids for alleviating inflammatory pain has been limited because of the variety of central nervous system (CNS) side-effects produced by opioids. There has been an interest in the preparation of peripherally-acting opioid agonists that have limited or no access to the CNS in an effort to reduce or eliminate these side-effects.

Introducing polar or charged groups into or onto these ligands has been attempted in order to enhance their CNS/peripheral nervous system (PNS) selectivity. However, polarization of the opioid may result in significant reduction in potency. For example, quaternization of opiate antagonists generally greatly diminishes their affinity for opiate receptors (Brown et al., Neuropharm. 24:181–192 (1985)). Methylnaloxone and methylnaltrexone possess only about 2 to 4% of the activity of their respective parent compounds. In addition, the polarized compound may produce effects unrelated to the activation or blockage of the opiate receptor. For example, quaternary naloxone produces tumors and convulsions at high dosages (Brown et al., cited above).

In addition, it has been shown that aspartic acid conjugates of opioid ligands naltrexamine and oxymorphamine cross the blood-brain barrier (BBB) poorly, as indicated by very large iv-icv dose ratios in mice (Botros et al., J. Med. Chem. 32:2068–2071 (1989) Portoghese (U.S. Pat. No. 4,806,556)). The poor CNS penetration of these conjugates was attributed to the highly charged nature of the zwitterionic group, which decreases the lipophilicity of the conjugates.

There have also been a limited number of reports of $\kappa$-selective agonists with restricted access to the CNS (Birch et al., Bioorg. Med. Chem. Lett. 2:1275–1278 (1992); Rogers et al., Br. J. Pharmacol. 106:783–789 (1992)). For example, ICI 204448, a 2-(3,4-dichlorophenyl)-N-methyl-N-[1-(phenyl)-2-(1-pyrrolidinyl)ethyl]acetamide derivative has been shown to produce peripheral antinociception in rat models of inflammation (Shaw et al., Br. J. Pharmacol. 96:986–992 (1989)).

Thus, a continuing need exists for selective and potent opioid ligands with high $\kappa$ receptor activity and low CNS penetration.

SUMMARY OF THE INVENTION

The invention provides compounds of the formula (I):

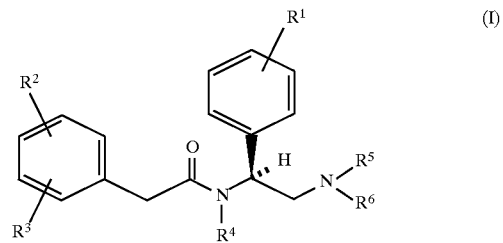

wherein
$R^2$ is H or halo;
$R^3$ is halo; or
$R^2$ and $R^3$ are at adjacent carbon atoms and together with those carbon atoms comprise a 5–7 membered aromatic or aliphatic ring fused with the phenyl ring, optionally comprising 1–2N, 1–2S or 1–2 nonperoxide O;
$R^4$ is ($C_1$–$C_4$) alkyl, preferably $CH_3$;
$R^5$ and $R^6$ are independently selected from ($C_1$–$C_4$) alkyl, or together with N are a 5–7 membered aromatic or aliphatic ring which may optionally comprise 1–2N, 1–2S or 1–2 nonperoxide O; where the ring may be optionally substituted with hydroxy($C_1$–$C_4$)alkyl or [($C_1$–$C_4$) alkyl]C=O;
$R^1$ is N($R^7$)C(O)—A(B)(C) wherein A is ($C_1$–$C_5$)alkyl, B is amino and C is H, OH, $CH_3$, $SR^8$, phenyl, 4-hydroxyphenyl, indol-3-yl, $CO_2R^8$, $SO_3R^8$, imidazol-3-yl, $CO_2N(R^8)_2$, $N(R^8)_2$ or guanidino, wherein each $R^8$ is H, benzyl, or ($C_1$–$C_4$)alkyl; or wherein A(B)(C) together are pyrrolidin-2-yl or 4-hydroxypyrrolidin-2-yl; or a pharmaceutically acceptable salt thereof.

In the group C(O)—A(B)(C), C(O) indicates a carbonyl group and B and C are attached to A independently, at the same or different positions. Preferably, the group C(O)—A(B)(C) is the residue of a naturally occurring amino acid. The term "naturally occurring amino acid" is defined as D, L, or DL-glycine, alanine, serine, threonine, valine, leucine, isoleucine, cysteine, cystine, cysteine, methionine, phenylalanine, tyrosine, proline, hydroxyproline, tryptophan, aspartic acid, glutamic acid, histidine, lysine, or argine, wherein the group N($R^7$)C(O) is an amido linkage formed between an amino acid carboxyl group and N($R^7$)H, as disclosed hereinbelow. Preferably, N($R^7$)C(O)—A(B)(C)

is the residue of a naturally occurring L-amino acid, such as those depicted in *Remington's Pharmaceutical Sciences*, A. Osol, ed., Mack Pub. (16th ed. 1980) at page 395. These include —N(R$^7$)C(O)CH(NH$_2$)(CH$_2$)$_{1-3}$CO$_2$R$^8$ or —N(R$^7$)C(O)(CH$_2$)$_{1-3}$CH(NH$_2$)CO$_2$R$^8$ wherein R$^7$ is (C$_1$–C$_4$)alkyl or H; and R$^8$ is (C$_1$–C$_4$)alkyl, benzyl, or H; or a pharmaceutically acceptable salt thereof.

In a particular embodiment, R$^2$ and R$^3$ are both halo groups, more preferably Cl. In a preferred embodiment, R$^2$ is at the 4-position and R$^3$ is at the 3-position of the phenyl ring.

Where R$^2$ and R$^3$ form a ring with two adjacent phenyl ring atoms, preferably R$^2$ and R$^3$ form a 5-membered ring, optionally substituted with N, S or O. For example, R$^2$ and R$^3$ together with the two phenyl carbon atoms may comprise a pyrrolyl, furanyl or thiophenyl ring. In a particular embodiment, where R$^2$ and R$^3$ form such a ring, preferably R$^3$ is at the 2-position and R$^2$ is at the 3-position of the phenyl ring. According to another embodiment, R$^2$ and R$^3$ together are 2,3-benzo.

In a further embodiment, R$^5$ and R$^6$ together with N form a saturated ring, e.g., a pyrrolidinyl or piperidinyl ring. Where R$^5$ and R$^6$ are a pyrrolidinyl ring, the compound may be substituted at the 3-position with CH$_2$OH, OH, CH$_3$CO or CHO.

The residue R$^1$ is preferably at the 3- or 4- position of the phenyl ring, and is preferably selected from a residue of an alpha-amino acid such as N(H)C(O)CH(NH$_2$)CH$_2$CO$_2$R$^8$, N(H)C(O)CH(NH$_2$)—(CH$_2$)$_2$—CO$_2$R$^8$, N(H)C(O)CH$_2$CH(NH$_2$)CO$_2$R$^8$, or N(H)C(O)CH$_2$CH$_2$CH(NH$_2$)CO$_2$R$^8$, wherein R$^8$ is H or (C$_1$–C$_4$)alkyl.

As shown in the figures above, the configuration of any other optically active center can be R, S or RS.

As used herein, the term "alkyl" includes linear or branched alkyl, cycloalkyl, or cycloalkylalkyl. Preferably, (C$_1$–C$_4$)alkyl is methyl. Halo includes Br, Cl, I, or F.

Preferably, the invention provides a kappa opioid receptor agonist of the formula (II)

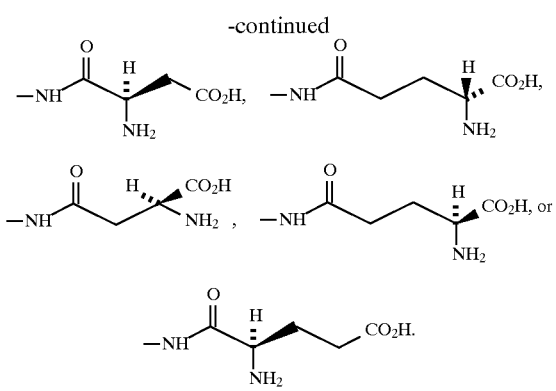

wherein R is N(R$^7$)C(O)—A(B)(C) wherein A is (C$_1$–C$_5$) alkyl, B is amino and C is H, OH, CH$_3$, SR$^8$, phenyl, 4-hydroxyphenyl, indol-3-yl, CO$_2$R$^8$, imidazol-3-yl, N(R$^8$)$_2$ or guanidino, wherein each R$^8$ is H, benzyl, or (C$_1$–C$_4$)alkyl, or whereinA(B)(C) together are pyrrolidin-2-yl or 4-hydroxypyrrolidin-2-yl. The preferred embodiments of R correspond to those defined for R$^1$, above.

Preferably, R or R$^1$ is:

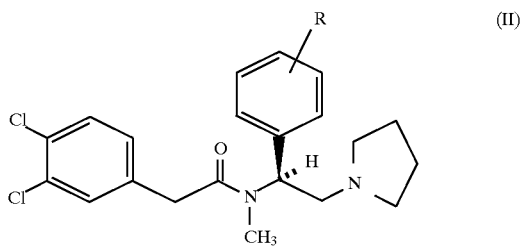

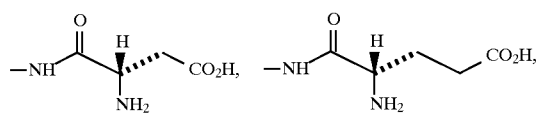

Pharmaceutically acceptable carboxylate or amine salts of the above are included within the scope of the invention as well.

These compounds are useful in alleviating the pain and suffering inflicted by chronic inflammatory diseases such as rheumatoid arthiritis as well as the treatment of gastrointestinal motility disorders such as ileus induced by surgery or peritonitis. A preferred utility is to produce peripheral analgesia without the CNS-mediated side effects of opioids. For example, the abdominal pain induced by laproscopic surgery can be reduced. Thus, methods of using the present compounds and pharmaceutical compositions comprising said compounds in combination with a pharmaceutically acceptable carrier are also written in the scope of the invention.

DETAILED DESCRIPTION

Figure 1:
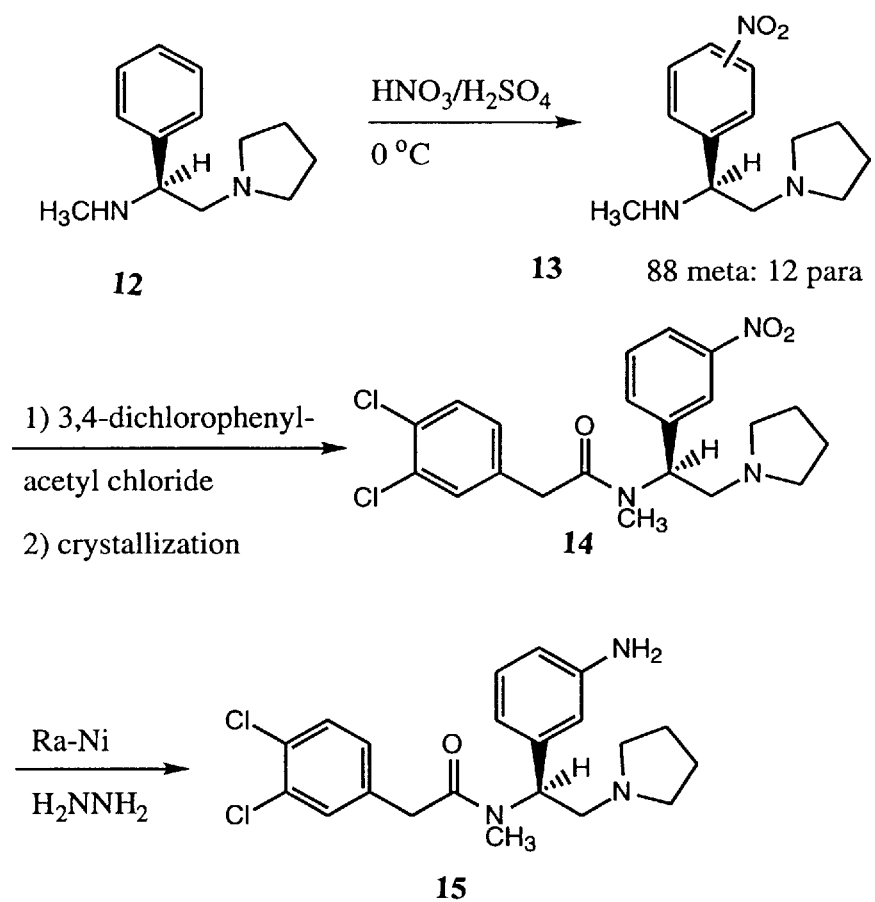
FIG. 1 is the synthetic scheme for 2-(3,4-dichlorophenyl)-N-methyl-N-[(1S)-1-(3-aminophenyl)-2-(1-pyrrolidinyl) ethyl]acetamide (15).

The present invention provides certain amino acid conjugates of 2-(3,4-dichlorophenyl)-N-methyl-N-[1-(phenyl)-2-(1-pyrrolidinyl)ethyl]acetamide (ICI 199441) (herein referred to as compound "3") useful for selectively activating the kappa opioid receptor.

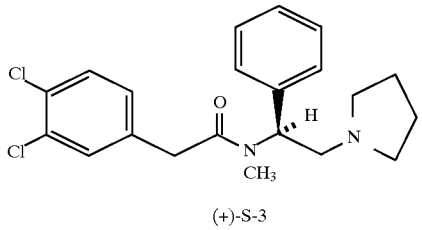

(+)-S-3

In a particular embodiment, the invention provides meta- and para-position substitutions on the unsubstituted phenyl ring of 3. In a preferred embodiment, the compounds of the invention are meta-position substituted. According to the present invention, the amino acid is derived from aspartic acid (Asp) and glutamic acid (Glu). In a particularly preferred embodiment, the amino acid conjugates are selected from 2-(3,4-dichlorophenyl)-N-methyl-N-{[1S]-1[N-(S-aspartic acid-α-amido)-3-aminophenyl]-2-[1-pyrrolidinyl]ethyl}acetamide (5), 2-(3,4-dichlorophenyl)-N-methyl-N-{[1S]-1[N-(R-aspartic acid-α-amido)-3-aminophenyl]-2-[1-pyrrolidinyl]ethyl}acetamide (6), 2-(3,4-dichlorophenyl)-N-Methyl-N-{[1S]-1[N-(S-aspartic acid-β-amido)-3-aminophenyl]-2-[1-pyrrolidinyl]ethyl}acetamide (7), 2-(3,4-dichlorophenyl)-N-methyl-N-{[1S]-1[N-(R-glutamic acid-α-amido)-3-aminophenyl]-2-[1-pyrrolidinyl]ethyl}acetamide (8), 2-(3,4-dichlorophenyl)-N-methyl-N-{[1S]-1[N-(S-glutamic acid-α-amido)-3-aminophenyl]-2-[1-pyrrolidinyl]ethyl}acetamide (9), 2-(3,4-dichlorophenyl)-N-methyl-N-{[1S]-1[N-(R-glutamic acid-γ-amido)-3-aminophenyl]-2-[1-pyrrolidinyl]ethyl}acetamide (10), and 2-(3,4-dichlorophenyl)-N-methyl-N-{[1S]-1[N-(S-glutamic acid-γ-amido)-3-aminophenyl]-2-[1-pyrrolidinyl]ethyl}acetamide (11).

In view of pronounced peripheral opioid analgesia at sites of inflammation, peripherally-acting opioid agonists of the invention can produce peripheral analgesia without the CNS-mediated side effects of opioids. A. Barber et al., *Med. Res. Rev.*, 12, 525 (1992). To produce peripherally-acting κ-selective agonist, zwitterionic groups or potential zwitterionic groups were introduced on the central phenyl group of 3. In general, substitutions at this phenyl group have minimal effect on receptor affinity and potency. In addition, the parent compound 3 is also advantageous as it is stereochemically simple and can be easily prepared from optically pure starting material. Moreover, L and D enantiomers of acidic amino acids, i.e., Asp and Glu, were attached to produce the meta-substituted amino-acid conjugates (5–11).

Both (+)-S-3 (ICI 199441) and its inactive enantiomer were prepared as previously reported (Costello et al., *J. Med. Chem.* 34:181–189 (1991); Barlow et al., *J. Med. Chem.* 34:3149–3158 (1991)). Methods for preparing analogs of 3 that may be generally useful to provide compounds of the present invention are described in the art. For example, replacement of the 3,4-dichlorophenyl ring with naphthyl, benzofuran or benzothiophene may be accomplished through modification of the methods described in Halfpenny et al., *J. Med. Chem.* 34:190–194 (1991); Clark et al., *J. Med. Chem.* 31:831–836 (1988) and Halfpenny et al., *J. Med. Chem.* 32:1620–1626 (1989). Procedures for preparing pyrrolidine ring modifications such as substitutions with hydroxymethylene (*J. Med Chem.* 32:1620–1626 (1989)) or hydroxyl or carbonyl groups (Scopes et al., *J. Med. Chem.* 35:490–501 (1992)) are also described.

In order to provide a moiety suitable for the attachment of amino acids, the meta-amino isomer 2-(3,4-dichlorophenyl)-N-methyl-N-[(1S)-1-(3-aminophenyl)-2-(1-pyrrolidinyl)ethyl]acetamide (15) was synthesized via the route depicted in FIG. 1 which afforded a regioisomeric mixture consisting of 88% m- and 12% p-nitro isomers (i.e., (13)). In order to attain product mixtures consisting of higher ratios of the m-$NO_2$ isomer (e.g., 95%), nitration is carried out at −45° C.

Figure 2:
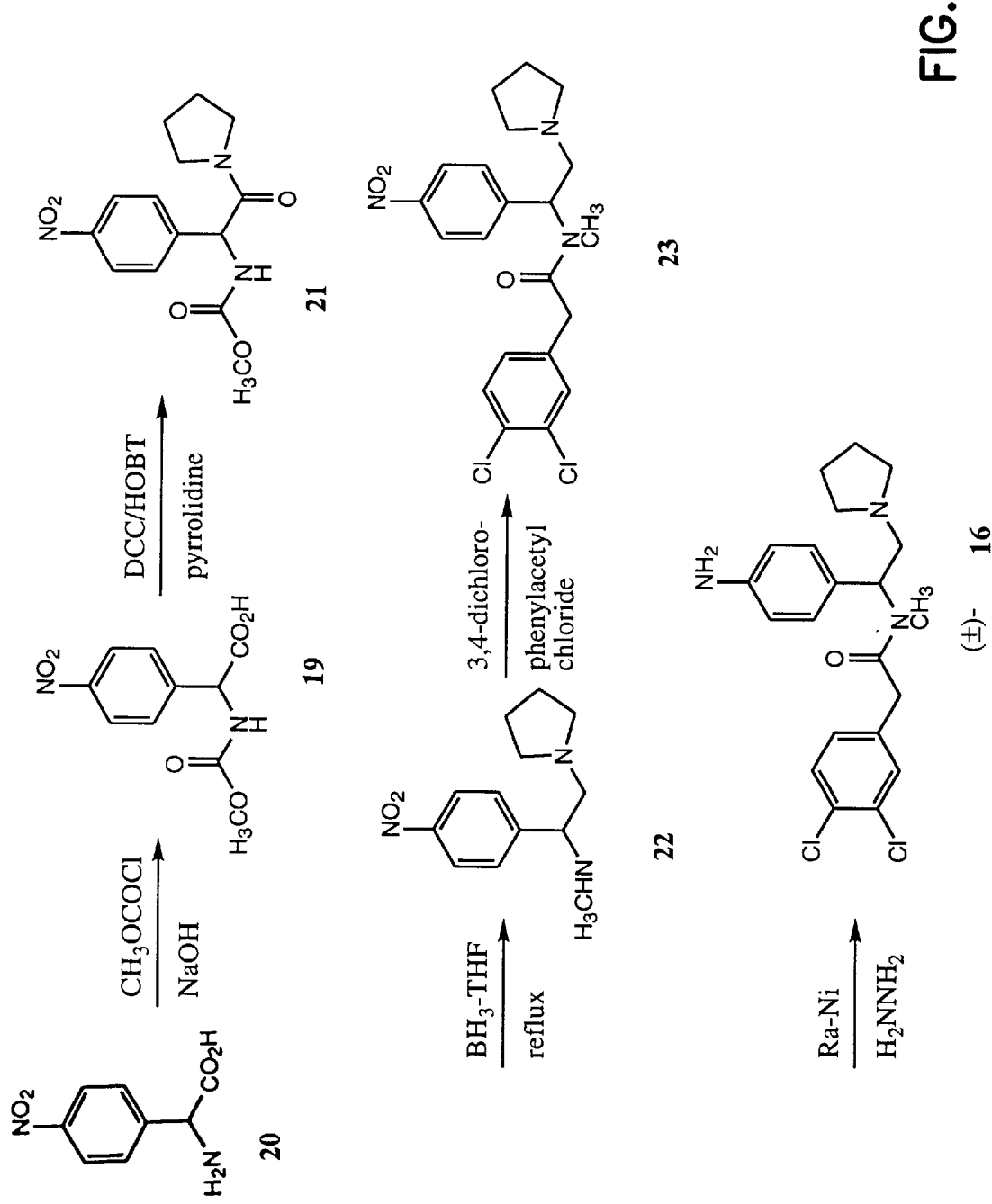
FIG. 2 is the synthetic scheme for 2-(3,4-dichlorophenyl)-N-methyl-N-[(1R,S)-1-(4-aminophenyl)-2-(1-pyrrolidinyl) ethyl]acetamide ((±)-16).

The para-substituted series of compounds were prepared as racemates beginning with (±)-16. Intermediate (±)-16 was prepared by a scheme analogous to that for the preparation of (+)-3 (FIG. 2). In addition, (+)-16 may be used as a starting material. (+)-16 is obtained by separation of a mixture of (+)-15 and (+)-16 via their brominated intermediates (17) and (18), respectively, as described in the Examples.

Figure 3:
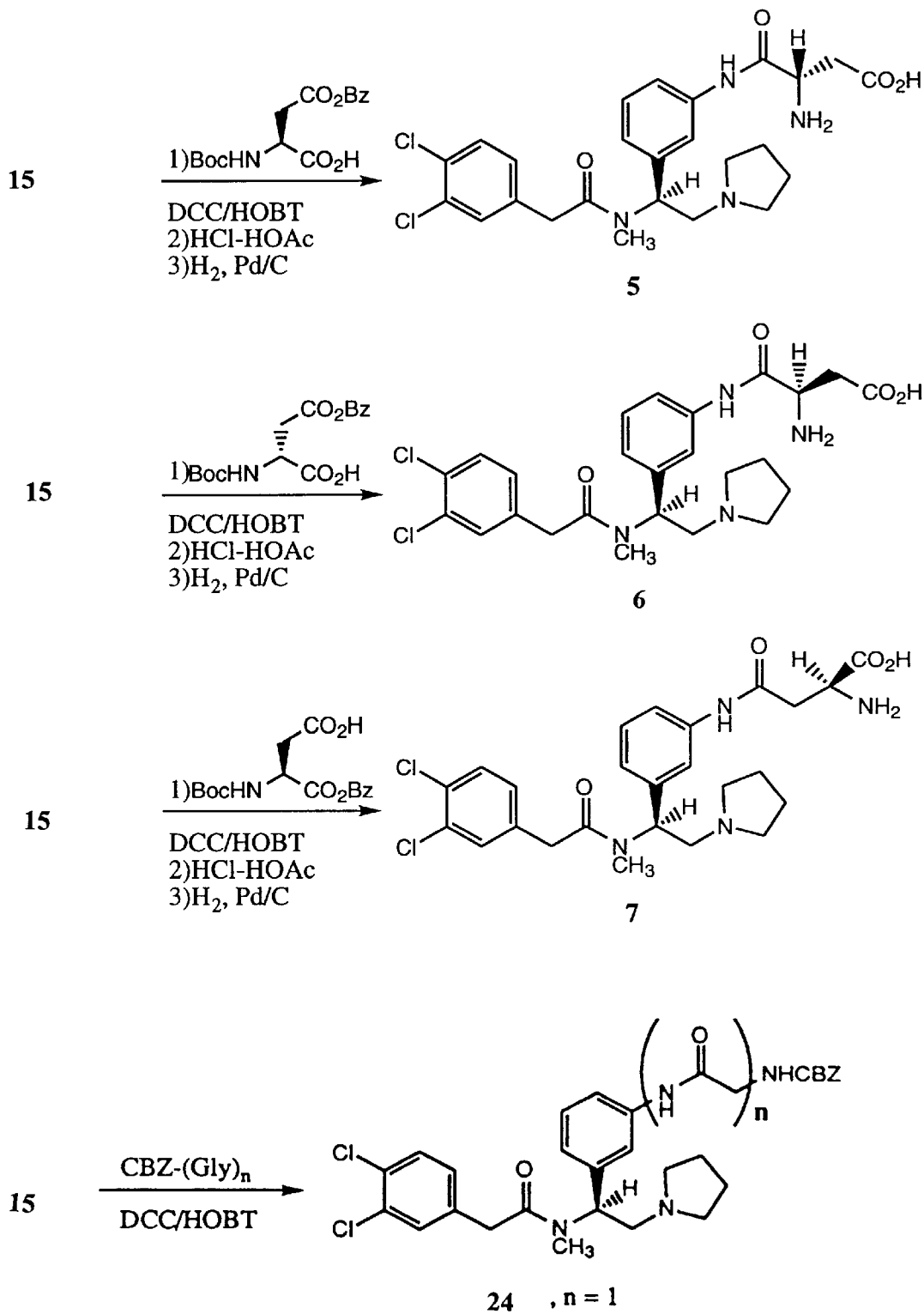
FIG. 3 shows the synthesis of 2-(3,4-dichlorophenyl)-N-methyl-N-{[1S]-1[N-(S-aspartic acid-α-amido)-3-aminophenyl]-2-[1-pyrrolidinyl]ethyl}acetamide (5), 2-(3,4-dichlorophenyl)-N-methyl-N-{[1S]-[1N-(R-aspartic acid-α-amido)-3-aminophenyl]-2-[1-pyrrolidinyl] ethyl}acetamide (6), 2-(3,4-dichlorophenyl)-N-methyl-N-{[1S]- 1[N-(S-aspartic acid-β-amido)-3-aminophenyl]-2-[1-pyrrolidinyl]ethyl}acetamide (7), and 2-(3,4-dichlorophenyl)-N-methyl-N-{[1S]-1-[N-CBZ-glycinamido)-3-aminophenyl]-2-[1-pyrrolidinyl]ethyl} acetamide (24).
Figure 4:
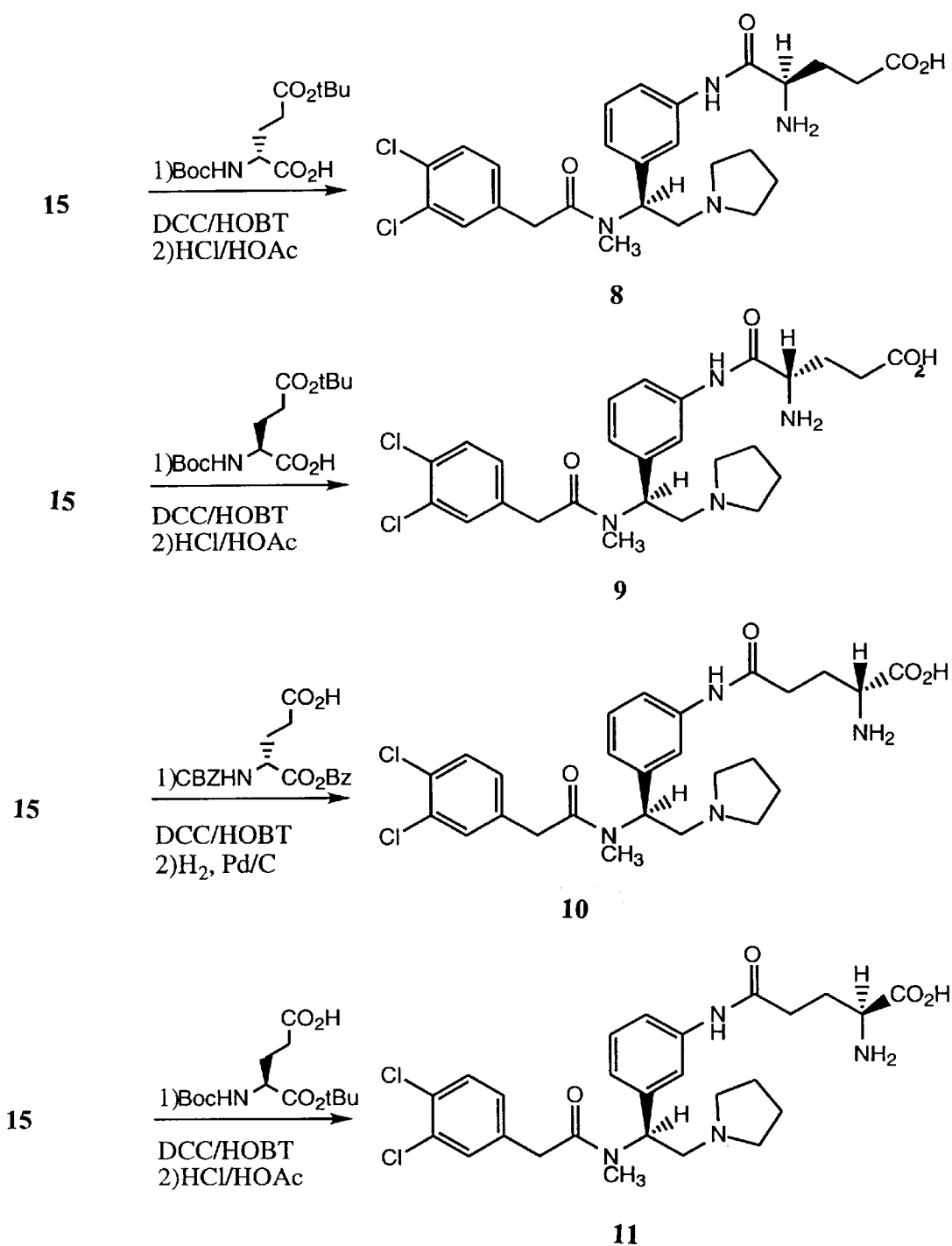
FIG. 4 shows the synthesis of 2-(3,4-dichlorophenyl)-N-methyl-N-{[1S]-1[N-(R-glutamic acid-α-amido)-3-aminophenyl]-2-[1-pyrrolidinyl]ethyl}acetamide (8), 2-(3,4-dichlorophenyl)-N-methyl-N-{[1S]-1[N-(S-glutamic acid-α-amido)-3-aminophenyl]-2-[1-pyrrolidinyl] ethyl}acetamide (9), 2-(3,4-dichlorophenyl)-N-methyl-N-{[1S]-1[N-(R-glutamic acid-γ-amido)-3-aminophenyl]-2-[1-pyrrolidinyl]ethyl}acetamide (10), and 2-(3,4-dichlorophenyl)-N-methyl-N-{[1S]-1[N-(S-glutamic acid-γ-amido)-3-aminophenyl]-2-[1-pyrrolidinyl] ethyl}acetamide (11).

Amino-acid conjugates 5–11 were prepared via DCC/(dicyclohexylcarbodiimide)HOBT(hydroxbenztriazol) coupling of the appropriately di-protected aspartic or glutamic acid to 15 (FIGS. 3 and 4). The di-protected amino-acid conjugates were purified by flash-column chromatography eluting with a $CH_2Cl_2$-based solvent system. In the case of the aspartate conjugates, the two different protecting groups were removed separately.

Suitably protected L- and D-aspartic acids were conjugated to 15 through the α-carboxyl group to produce 5 and 6, respectively (FIG. 3). Similarly, L-aspartic acid was conjugated to 15 via the β-carboxyl group to afford 7. Intermediate 15 was coupled to suitably protected L- and D-glutamic acids to yield the α-conjugates, 8 (52%) and 9 (72%), and the γ-conjugates, 10 (56%) and 11 (78%) (FIG. 4).

The amino acid conjugates of the present invention may be used to selectively bind to and activate κ opioid receptors producing analgesia with minimum physical dependence and respiratory depression. The conjugates can be used in alleviating the pain and suffering inflicted by chronic inflammatory diseases such as rheumatoid arthritis as well as the treatment of gastrointestinal motility disorders such as ileus induced by surgery or peritonitis, including the pain due to laproscopic surgery. Furthermore, attachment of the highly charged zwitterionic group limits diffusion of the receptor agonist across the blood-brain barrier, in comparison with the parent compound, thus reducing the CNS side effects normally associated with opioids.

The invention also comprises the pharmaceutically acceptable salts of the biologically active compounds of Formula I. Pharmaceutically acceptable amine salts may be salts of organic acids, such as acetic, citric, lactic, malic, tartaric, p-toluene sulfonic acid, methane sulfonic acid, and the like as well as salts of pharmaceutically acceptable mineral acids such as phosphoric, hydrochloric or sulfuric acid, and the like. Physiologically acceptable carboxylic acid salts include alkali metal carboxylates and quaternatery ammonium salts. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Although the compounds of the present invention and/or its salts may be administered as the pure chemicals, it is preferable to present the active ingredient as a pharmaceutical composition. The invention thus further provides a pharmaceutical composition comprising one or more of the claimed compounds and/or a pharmaceutically acceptable salt thereof, together with one or more pharmaceutically acceptable carriers therefor and, optionally, other therapeutic and/or prophylactic ingredients. The carrier(s) must be 'acceptable' in the sense of being compatible with the other ingredients of the composition and not deleterious to the recipient thereof.

Pharmaceutical compositions include those suitable for oral or parenteral (including intramuscular, subcutaneous and intravenous) administration. Forms suitable for parenteral administration also include forms suitable for administration by inhalation or insufflation or for nasal, or topical (including buccal, rectal, vaginal and sublingual) administration. The compositions may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combination thereof, and then, if necessary, shaping the product into the desired delivery system.

Pharmaceutical compositions suitable for oral administration may be presented as discrete unit dosage forms such as hard or soft gelatin capsules, cachets or tablets each containing a predetermined amount of the active ingredient; as a powder or as granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art., i.e., with enteric coatings.

Oral liquid preparations may be in the form of, for example, aqueous or oily suspension, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservative.

The compounds according to the invention may also be formulated for parenteral administration (e.g., by injection, for example, bolus injection or continuous infusion) and may be presented in unit dose form in ampules, pre-filled syringes, small bolus infusion containers or in multi-does containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds of the present invention may be formulated as ointments, creams or lotions, or as the active ingredient of a transdermal patch. Suitable transdermal delivery systems are disclosed, for example, in Fisher et al. (U.S. Pat. No. 4,788,603) or Bawas et al. (U.S. Pat. Nos. 4,931,279, 4,668,504 and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredient can also be delivered via iontophoresis, e.g., as disclosed in U.S. Pat. Nos. 4,140,122, 4,383,529, or 4,051,842.

Compositions suitable for topical administration in the mouth include unit dosage forms such as lozenges comprising active ingredient in a flavored base, usually sucrose and acadia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the above-described compositions can be adapted to provide sustained release of the active ingredient employed, e.g., by combination thereof with certain hydrophilic polymer matrices, e.g., comprising natural gels, synthetic polymer gels or mixtures thereof.

Pharmaceutical compositions suitable for rectal administration wherein the carrier is a solid are most preferably presented as unit dose suppositories. Suitable carriers include cocoa butter and other material commonly used in the art, and the suppositories may be conveniently formed by a mixture of the active compound with the softened or melted carrier(s) followed by chilling and shaping in molds.

For administration by inhalation, the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds according to the invention may take the form of a dry powder composition, for example, a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

For intra-nasal administration, a compound of the invention may be administered via a liquid spray, such as via a plastic bottle atomizer. Typical of these are the Mistometer® (Wintrop) and the Medihaler® (Riker).

For topical administration to the eye, the presently described compounds can be administered as drops, gels (see Chrai et al., U.S. Pat. No. 4,255,415), gums (see Lin et al., U.S. Pat. No. 4,136,177) or via a prolonged-release ocular insert (see Michaels, U.S. Pat. No. 3,867,519; Haddad et al., U.S. Pat. No. 3,870,791).

The pharmaceutical compositions according to the invention may also contain other adjuvants such as flavorings, coloring, antimicrobial agents, or preservatives.

It will be further appreciated that the amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

EXAMPLES

All NMR spectra were recorded on a GE 300 MHz spectrometer or a Varian-500 MHz spectrometer at room temperature. IR spectra were recorded with a Nicolet 5DXC FT-IR spectrometer. Optical rotations were measured using a Rudolph Research Autopol III automatic polarimeter. Melting points were determined using a Thomas Hoover capillary melting point apparatus and are uncorrected. Elemental analyses were conducted by M-H-W Laboratories in Phoenix, Ariz. Mass spectra were recorded by the Chemistry Mass Spec Labs at the University of Minnesota's Chemistry Department.

Example I (S)-1-[2-(Methylamino)-2-(3/4-nitrophenyl)ethyl]pyrrolidine (13)

To an ice-cold solution of 12 (Costello et al., *J. Med.Chem.*, 34, 181–189 (1991)) (21.3 g, 104 mmol) in concentrated sulfuric acid (150 mL) was added concentrated nitric acid (10 mL, 157 mmol) with vigorous stirring. The stirring with ice-cooling continued for 45 min, and the reaction mixture was made basic by careful addition of 5N NaOH and NaOH(s) pellets and water with stirring and ice-cooling. The precipitate was then extracted into EtOAc (3 L), which was dried ($MgSO_4$), filtered, evaporated under reduced pressure, and dried in vacuo to yield 22.06 g (85%) of an oil, which was used without further purification. Based on $^1$H NMR integration ratios, the product was determined to be a mixture of 88% meta- and 12% para-nitro regioisomers, and no peaks corresponding to the ortho-nitro isomer were observed: $^1$H NMR (free base, $CDCl_3$) δ 1.75 (br s, 4H, —$CH_2CH_2$—), δ 2.26 (s, 3H, $NCH_3$), δ 2.23–2.79 (complex, 7H, 3 $CH_2N$ and 1 NH), δ 3.64–3.69 (d of d, J=11 Hz, 3.6 Hz, 1H, CH), δ 7.47 (m, 1H, m-$NO_2C_6H_4$), δ 7.52 (d, J=8.4 Hz, p-$NO_2C_6H_4$, 12%), δ 7.71 (d, J=8.7 Hz, 1H, m-$NO_2C_6H_4$), δ 8.08 (d, J=8.4 Hz, 1H, m-$NO_2C_6H_4$), δ 8.15 (d, J=8.7 Hz, p-$NO_2C_6H_4$, 12%), δ 8.21 (br s, 1H, m-$NO_2C_6H_4$). MS (EI) m/z 250.2.

Example II 2-(3,4-Dichlorophenyl)-N-methyl-N-[(1S)-1-(3-nitrophenyl)-2-(1-pyrrolidinyl)ethyl]acetamide (14)

A solution of 3,4-dichlorophenylacetic acid (23.59 g, 115 mmol) in thionyl chloride (66 mL, 905 mmol) was heated at 76° C. for 2.5 h and then evaporated under reduced pressure to yield 3,4-dichlorophenylacetyl chloride. A solution of 3,4-dichlorophenylacetyl chloride in cold, dry $CH_2Cl_2$ (90 mL) was added dropwise to an ice-cold solution of 13 (26.025 g, 104 mmol) and $Et_3N$ (16 mL, 115 mmol) in dry $CH_2Cl_2$ (150 mL) with stirring under argon and ice-cooling over 30 min. The mixture was stirred at 25° C. for 21 h before the solvent was removed under reduced pressure. The residue was then dissolved in EtOAc and washed with 3N NaOH. The organic fraction was dried ($MgSO_4$), filtered, and evaporated to yield 43.5 g (95%) of crude product. Two crystallizations from boiling MeOH yielded 14.HCl (10.24 g, 21%): mp (14.HCl)>260° C.; $[α]_D^{25°\,C.}$+137° (c=0.2, 14.HCl:, MeOH); $^1$H NMR (14.HCl, DMSO-$d_6$) δ 1.89–2.01 (m, 4H, —$CH_2CH_2$—), δ 2.83 (s, 3H, $NCH_3$), δ 3.15–4.19 (complex, 6H, 3 —$CH_2N$), δ 3.85 (d, J=17 Hz, 1H, $ArCH_2CO$), δ 3.99 (d, J=16 Hz, 1H, $ArCH_2CO$), δ 6.21 (m, 1H, CH), δ 7.28–7.30 (m, 1H, $Cl_2C_6H_3$—), δ 7.56–7.57 (m, 2H, $Cl_2C_6H_3$—), δ 7.71–7.72 (m, 2H, m-$NO_2C_6H_4$), δ 8.08 (s, 1H, m-$NO_2C_6H_4$), δ 8.21–8.22 (m, 1H, m-$NO_2C_6H_4$). MS (FAB) m/z 436.1. Anal. ($C_{21}H_{23}N_3O_3Cl_2$.HCl.0.5 $H_2O$) calcd.: C 52.35, H 5.23, N 8.72, Cl 22.08; found: C 52.18, H 5.22, N 8.58, Cl 22.00.

Example III 2-(3,4-Dichlorophenyl)-N-methyl-N-[(1S)-1-(3-aminophenyl)-2-(1-pyrrolidinyl)ethyl]acetamide (15)

A mixture of 14 (1.17 g, 2.68 mmol), hydrazine (1 mL, 32 mmol), and Raney-Ni in 95% EtOH (75 mL) was heated at 55° C. Small portions of Raney-Ni and hydrazine were added until TLC indicated completion of the reaction (2.5 h). The reaction was filtered through celite, and the Raney-Ni was washed with hot MeOH. The combined filtrates were evaporated under reduced pressure to yield 15 in quantitative yield. Further purification was achieved by gravity column chromatography with $CHCl_3$:1% MeOH:2% $NH_3$:mp (15.2HCl) softens at 149° C. and melts at 223°–224° C.; $[α]_D^{25°\,C.}$+143.7° (c=0.45, 15.2HCl, MeOH); $^1$H NMR (15.2HCl, DMSO-$d_6$) δ 1.9–2.0 (m, 4H, —$CH_2CH_2$—), δ 2.82 (s, 3H, $NCH_3$), δ 3.07–4.07 (complex, 6H, 3 —$CH_2N$), δ 3.77 (d, J=16 Hz, 1H, $ArCH_2CO$), δ 4.10 (d, J=16 Hz, 1H, $ArCH_2CO$), δ 6.05 (d of d, J=12.5 Hz and 2.5 Hz, 1H, CH), δ 6.87 (br s, 2H, m-$NH_2C_6H_4$), δ 6.92 (d, J=8 Hz, 1H, m-$NH_2C_6H_4$), δ 7.26 (t, J=8 Hz, 1H, m-$NH_2C_6H_4$), δ 7.29–7.31 (m, 1H, $Cl_2C_6H_3$—), δ 7.55–7.59 (m, 2H, $Cl_2C_6H_3$—). MS (FAB) m/z 406.2. Anal. ($C_{21}H_{25}N_3OCl_2$.2HCl) calcd.: C 52.62, H 5.68, N 8.77, Cl 29.59; found: C 52.43, H 5.58, N 8.50, Cl 29.47.

EXAMPLE IV 2-(3,4-Dichlorophenyl)-N-methyl-N-[(1S)-1-(5-amino-2,4-dibromophenyl)-2-(1-pyrrolidinyl)ethyl]acetamide (17) and 2-(3,4-dichlorophenyl)-N-methyl-N-[(1S)-1-(4-amino-3,5-dibromophenyl)-2-(1-pyrrolidinyl)ethyl]acetamide (18)

With stirring at 25° C. under Ar, a solution of $Br_2$ (1) (0.63 mL, 12.23 mmol) in AcOH (20 mL) was added dropwise over 30 min to the solution of an approximately 85:15 mixture of (+)-15 and (+)-16 (1.6565 g, 4.0766 mmol) in of AcOH (110 mL) and of $Et_3N$ (1.14 mL). After 30 min, the reaction mixture was poured into a mixture of crushed ice and conc. $NH_4OH$ (300 mL), and the aqueous fraction was extracted with $CHCl_3$ (600 mL), which was dried ($Na_2SO_4$), filtered through celite, and evaporated. The crude product was then gravity-column chromatographed eluting with $CHCl_3$:2% $NH_3$:2% MeOH to yield 17 (0.8729 g, 45% of theoretical based on a 85:15 mixture). The fractions containing 18 were combined and gravity-column chromatographed again eluting with $CHCl_3$:2% MeOH to yield 18 (0.2648 g, 77% of theoretical based on a 85:15 mixture). The yield of 18 is based on pure fractions obtained from column and is not optimized.

17.2HCl: $^1$H NMR (DMSO-d$_6$-2 dr D$_2$O) δ 1.8–2.0 (m, 4H, —CH$_2$CH$_2$—), 2.6 (s, 3H, —NCH$_3$), 3.0–4.0 (complex, 8H, 4 —CH$_2$—), 5.80 (m, 1H, —CH—), 6.81 (s, 1H, Br$_2$-NH$_2$-C$_6$H$_2$—), 7.17 (m, 1H, Cl$_2$C$_6$H$_3$—), 7.41 (d, J=1.8 Hz, Cl$_2$C$_6$H$_3$—), 7.46 (d, J=7.8 Hz, Cl$_2$C$_6$H$_3$—), 7.56 (s, 0.6H, Br$_2$—NH$_2$—C$_6$H$_2$—), 8.10 (s, 0.18H). MS (FAB) m/z 564.0.

18: $^1$H NMR (CDCl$_3$) δ 1.70 (br s, 4H, —CH$_2$CH$_2$—), 2.65 (s, 3H, —NCH$_3$—), 2.4–2.7 (complex, 4H, —N(CH$_2$)$_2$), 3.02 (m, 1H, —CHCH$_2$N—), 3.60–3.78 (m, 3H, —CH$_2$CON— and —CHCH$_2$N—), 4.53 (br s, 2H, —NH$_2$), 5.90 (m, 1H, —CH—), 7.10–7.12 (m, 1H, Cl$_2$C$_6$H$_3$—), 7.25 (s, 2H, Br$_2$—NH$_2$—C$_6$H$_2$—), 7.30–7.36 (m, 2H, Cl$_2$C$_6$H$_3$—). MS (FAB) m/z 564.1.

Hydrogenation of 17. A mixture of 17 (0.3864 g, 0.6849 mmol) and 190 mg of 10% Pd/C in 12 mL of MeOH was hydrogenated at 25° C. under 15 psi for 24 h before the mixture was filtered through packed celite, and the Pd/C was washed thoroughly with hot MeOH (125 mL). The combined filtrate was then evaporated under reduced pressure to yield 152 HBr (0.3820 g, 98%). The yield is also quantitative when the hydrogenation is done at a small scale (30 mg).

Hydrogenation of 18. Intermediate 18 (0.2648 g, 0.4694 mmol) was hydrogenated in a similar manner to yield (+)-16.2HCl (0.1342 g, 60%) after gravity-column chromatography eluting with CHCl$_3$:2% NH$_3$:2% MeOH: mp 150° C. (dec); [α]$_{25° C.}$ +141° (c=0.21, MeOH); $^1$H NMR is identical to that of (±)-16. MS (FAB) m/z 406.2. Anal. (C$_{21}$H$_{25}$N$_3$OCl$_2$.2HCl) calcd.: C 52.62, H 5.68, N 8.77; found: C 52.84, H 5.63, N 8.61.

Example V (±)-N-(methoxycarbonyl)-2-(4-nitrophenyl)glycine (19)

To a stirred mixture of (±)-2-(4-nitrophenyl)glycine (20) (Heyns et al., *Justus Lieberg's Annalen der Chimie* 611:55–56 (1958)) (3.2400 g, 16.5 mmol) and NaOH (0.6611 g, 16.5 mmol) in water (150 mL) were added methyl chloroformate (1.404 mL, 18.2 mmol), 2N NaOH (9.1 mL), and water (6 mL) at 0° C. After adjusting pH to 9 with 2N NaOH (1 mL) and stirring at 25° C. for 17 h, the mixture was basified to pH 10 with 2N NaOH and washed with diethyl ether before it was acidified with 5N HCl in the presence of EtOAc. The organic fractions (1 L) were dried (MgSO$_4$) and evaporated to yield 19 (3.62 g, 86%): mp 152° C.; $^1$H NMR (DMSO-d$_6$) δ 3.53 (s, 3H, OCH$_3$), 5.35 (d, J=8.7 Hz, 1H, CH), 7.66 (d, J=8.4 Hz, 2H, aromatic), 8.20 (d, J=8.4 Hz, 3H, aromatic and NH). MS (FAB) m/z 255.0.

Example VI (±)-Methyl-N-[(4-nitrophenyl)(1-pyrrolidinylcarbonyl)-methyl] carbamate (21)

To a suspension of 19 (1.0049 g, 3.95 mmol) in dry CH$_2$Cl$_2$ was added 1-hydroxybenzotriazole (HOBT) (0.5394 g, 3.99 mmol) with ice-cooling and stirring under a N$_2$ atmosphere. A CH$_2$Cl$_2$ solution of dicyclohexylcarbodiimide (DCC) (0.8314 g, 4.03 mmol) was added dropwise, and the reaction mixture was stirred in ice-bath for 1 h before pyrrolidine (0.330 mL, 3.95 mmol) was added. After stirring at 25° C. for 5 days, the reaction mixture was filtered through celite, and the residue remaining after evaporation of the filtrate was dissolved in EtOAc and washed sequentially with saturated NaHCO$_3$, brine, 2N HCl, and brine. The organic fraction was dried (MgSO$_4$) and evaporated to yield 21 (1.193 g, 98%): mp 143–145° C.; $^1$H NMR (CDCl$_3$) δ 1.69–1.94 (m, 4H, CH$_2$CH$_2$), 3.00–3.60 (complex, 4H, CH$_2$NCH$_2$), 3.63 (s, 3H, OCH$_3$), 5.45 (d, J=6 Hz, 1H, CH), 6.42 (d, J=6 Hz, 1H, NH), 7.61 (d, J=8.4 Hz, 2H, aromatic), 8.20 (d, J=8.4 Hz, 2H, aromatic). MS (FAB) m/z 307.1.

Example VII (±)-1- [2-(Methylamino)-2-(4-nitrophenyl)ethyl] pyrrolidine (22)

A solution of 21 (3.0354 g, 9.88 mmol) in dry THF (66 mL) was added dropwise to 1M BH$_3$-THF in THF (49.5 mL, 49.5 mmol) with stirring under N$_2$ and cooling in ice-bath. After refluxing for 96 h, excess BH$_3$-THF was hydrolyzed with concentrated HCl, and the reaction mixture was stirred at 40° C. for 2.5 h before it was evaporated. The residue was then partitioned between 2N HCl and CHCl$_3$, followed by basification of the aqueous fraction with NaOH(s) and extraction with diethyl ether. After drying (MgSO$_4$) and evaporating the ether fractions, the product was purified by flash column chromatography (CHCl$_3$:1% MeOH:2% NH$_3$, R$_f$=0.19). The yield after purification was 1.22 g (49.7%): $^1$H NMR (CDCl$_3$) δ 1.75 (br s, 4H, CH$_2$CH$_2$), 2.22–2.76 (complex, 6H, 3 CH$_2$N), 2.26 (s, 3H, NCH$_3$), 3.66 (d of d, J=9.9 Hz and 3.6 Hz, 1H, CH), 7.52 (d, J=8.4 Hz, 2H, aromatic), 8.15 (d, J=8.7 Hz, 2H, aromatic). MS (FAB) m/z 249.2.

Example VII 2-(3,4-Dichlorophenyl)-N-methyl-N-[(1R,S)-1-(4-nitrophenyl)-2-(1-pyrrolidinyl)ethyl]acetamide (23)

Compound 23 was prepared from 22 by a method similar to the preparation of 14 using 3,4-dichlorophenylacetyl chloride and Et$_3$N in dry CH$_2$Cl$_2$. The crude product was purified by flash column chromatography using CHCl$_3$:2% NH$_3$:0.9% MeOH as solvent (R$_f$=0.2). Crude products from two experiments were combined for the purification, which resulted in recrystallization of 0.90 g (30%) of 23.HCl (based on a combined theoretical yield of both experiments): mp 254° C. (23.HCl); $^1$H NMR (free base, CDCl$_3$) δ 1.75 (br s, 4H, CH$_2$CH$_2$), 2.42–3.14 (complex, 6H, 3 CH$_2$N), 2.74 (s, 3H, NCH$_3$), 3.69 (d, J=15.6 Hz, 1H, ArCH$_2$CO), 3.78 (d, J=15.9 Hz, 1H, ArCH$_2$CO), 6.10 (d of d, J=9.8 Hz and 6 Hz, 1H, CH), 7.12–7.35 (complex, 3H, —C$_6$H$_3$Cl$_2$), 7.46 (d, J=8.4 Hz, 2H, —C$_6$H$_4$NO$_2$), 8.16 (d, J=8.7 Hz, 2H, —C$_6$H$_4$NO$_2$); $^{13}$C NMR (23.HCl, DMSO-d$_6$) δ 23.8, 24.2, 31.4, 52.3, 53.6, 56.3, 124.7, 129.8, 130.0, 131.0, 131.4, 131.8, 133.2, 138.4, 145.3, 148.2, 173.3. MS (FAB) m/z 436.2. Anal. (C$_{21}$H$_{23}$N$_3$O$_3$Cl$_2$.HCl) calcd.: C 53.35, H 5.12, N 8.89, Cl 22.50; found: C 53.48, H 5.01, N 8.85, Cl 22.38.

Example IX 2-(3,4-dichlorophenyl)-N-methyl-N-[(1R,S)-1-(4-aminophenyl)-2-(1-pyrrolidinyl)ethyl]acetamide (±)-16)

Compound (±)-16 was prepared from 23 by a method similar to the preparation of 15 using Raney nickel and hydrazine to yield (±)-16 (0.11 g, 59%): mp ((±)-16.2HCl) 159°–161° C.; $^1$H NMR (free base, CDCl$_3$) δ 1.77 (br s, 4H, CH$_2$CH$_2$), 2.46–3.22 (complex, 6H, 3 CH$_2$N), 2.69 (s, 3H, NCH$_3$), 3.67 (d, J=15.9, 1H, ArCH$_2$CO), 3.78 (d, J=14.4 Hz, 1H, ArCH$_2$CO), 6.03 (d of d, J=11.7 and 6 Hz, 1H, CH), 6.64 (d, J=8.4 Hz, 2H, —C$_6$H$_4$NH$_2$), 7.09 (d, J=8.4 Hz, 2H, —C$_6$H$_4$NH$_2$), 7.15–7.39 (complex, 3H, —C$_6$H$_3$Cl$_2$); $^{13}$C NMR (±)-16.2HCl, DMSO-d$_6$) δ 23.75, 24.15, 51.86, 53.54, 53.60, 56.24, 122.28, 122.36, 129.55, 129.92, 131.00, 131.34, 131.78, 133.18, 133.23, 138.61, 173.04. MS (FAB) m/z 406.2. Anal. (C$_{21}$H$_{25}$N$_3$OCl$_2$.2HCl) calcd.: C 52.62, H 5.68, N 8.77, Cl 29.59; found: C 52.54, H 5.68, N 8.53, Cl 29.40.

Example XI

2-(3,4-Dichlorophenyl)-N-methyl-N-{[1S]-1-[N-(S-aspartic acid-α-amido)-3-aminophenyl]-2-[1-pyrrolidinyl]ethyl}acetamide (5)

To an ice-cold mixture of N-t-Boc-L-aspartic acid-β-benzyl ester (0.3541 g, 1.095 mmol) and HOBT (0.1495 g, 1.106 mmol) in dry CH$_2$Cl$_2$ (20 mL) was added with stirring under N$_2$ a solution of DCC (0.2331 g, 1.130 mmol) in dry CH$_2$Cl$_2$ (10 mL). After stirring for 1 h at 0° C., a solution of 15 (0.2228 g, 0.5483 mmol) in dry CH$_2$Cl$_2$ (6 mL) was added, and the reaction mixture was stirred at 25° C. under N$_2$ for 23 h before it was filtered. The filtrate was then washed with saturated NaHCO$_3$ before it was dried (Na$_2$SO$_4$), filtered, and evaporated under reduced pressure. Flash-column chromatography with CHCl$_3$:2% NH$_3$:2% MeOH yielded 0.3315 g (85%) of the protected intermediate, which was further purified on hplc using CHCl$_3$:2% NH$_3$:1% MeOH. After stirring the protected intermediate (0.0905 g, 0.1272 mmol) in 1 mL of 2N HCl, 1 mL of AcOH, and 1 drop of anisole at 25° C. for 20 min, 2 mL of MeOH and some 10% Pd/C were added, and the mixture was hydrogenated at 25° C. using a hydrogen balloon. After 1 h, some more Pd/C were added, and 20 min later the mixture was filtered through celite and evaporated in vacuo. The clear film which remained was converted to a white solid by addition of iPrOH and evaporation to dryness in vacuo to yield 5.2HCl (50.6 mg, 66.9%): mp 170° C. (decomp); [α]$_D^{25°\ C.}$+113° (c=0.2, MeOH); $^1$H NMR (DMSO-d$_6$) δ 1.97 (br s, 4H, —CH$_2$CH$_2$—), δ 2.82 (s, 3H, NCH$_3$), δ 2.85–4.23 (complex, 11H, 5 —CH$_2$— and 1 —CH—), δ 6.10 (m, 1H, —CH—), δ 7.04–7.67 (complex, 7H, aromatic), δ 8.3 (s, 1H, amide NH), δ 8.2–8.8 (br s, 3H, NH$_3$), δ 10.6–10.8 (br s, 2H, NH, CO$_2$H). MS (FAB) m/z 521.3. Anal. (C$_{25}$H$_{30}$N$_4$O$_4$Cl$_2$.2HCl) calcd.: C 50.52, H 5.43, N 9.43, Cl 23.86; found: C 50.35, H 5.69, N 9.16, Cl 23.66.

Example XII

2-(3,4-Dichlorophenyl)-N-methyl-N-{[1S]-1-[N-(R-aspartic acid-α-amido)-3-aminophenyl]-2-[1-pyrrolidinyl]ethyl}acetamide (6)

Compound 6 was prepared from 15 (0.2259 g, 0.5559 mmol), N-t-Boc-D-aspartic acid-β-benzyl ester (0.3598 g, 1.113 mmol), HOBT (0.1520 g, 1.125 mmol), and DCC (0.2363 g, 1.145 mmol) in dry CH$_2$Cl$_2$ (23 mL). The procedure and reaction conditions are similar to those employed for the preparation of 5. After 23 h, the reaction was worked up similar to that of 5, and purification by flash-column chromatography with CH$_2$Cl$_2$:2% NH$_3$:3% MeOH yielded 0.3845 g (97%) of the protected intermediate, which eluted off the hplc as a single sharp peak with CHCl$_3$:2% NH$_3$:1% MeOH. After stirring the protected intermediate in 2N HCl (3mL), AcOH (3 mL), and 2 drops of anisole at 25° C. for 1 h, the mixture was evaporated in vacuo, and the residue was partitioned between CH$_2$Cl$_2$ and saturated NaHCO$_3$. The organic fraction was dried (Na$_2$SO4), filtered through celite, and evaporated to yield the benzyl ester intermediate which was purified by gravity-column chromatography with CH$_2$Cl$_2$:2% NH$_3$:3% MeOH. The benzyl ester intermediate was then converted to the 2HCl salt with EtO.HCl and hydrogenated at 40 psi with 35 mg of 10% Pd/C in MeOH (8 mL). After 45 min, the mixture was filtered through celite, and the Pd/C was washed thoroughly with hot MeOH. The solvent from the combined filtrates was removed, the residue was then taken up in iPrOH, and the solvent was evaporated to yield 6.2HCl (0.1012 g, 30.6%): mp 200° C. (decomposes); [α]$_D^{25°\ C.}$+ 103.9° (c=0.23, MeOH); $^1$H NMR (DMSO-d$_6$) δ 1.94 (br s, 4H, —CH$_2$CH$_2$—), δ 2.808 (s, 3H, NCH$_3$), δ 2.77–4.24 (complex, 11H, 5 —CH$_2$— and 1 —CH—), δ 6.076 (m, 1H, —CH—), δ 7.014–7.658 (complex, 7H, aromatic), δ 8.6 (br s, exchangeable proton), δ 10.9 (br s, exchangeable proton). MS (FAB) m/z 521.2. Anal. (C$_{25}$H$_{30}$N$_4$O$_4$Cl$_2$.2HCl) calcd.: C 50.52, H 5.43, N 9.43, Cl 23.86; found: C 50.41, H 5.48, N 9.24, Cl 23.66.

Example XIII

2-(3,4-Dichlorophenyl)-N-methyl-N-{[1S]-1-[N-(S-aspartic Acid-b-amido)-3-Aminophenyl]-2-[1-Pyrrolidinyl]ethyl}acetamide (7)

Compound 7 was prepared from 15 (0.2379 g, 0.5855 mmol), N-t-Boc-L-aspartic acid-α-benzyl ester (1.8933 g, 5.855 mmol), HOBT (0.8070 g, 5.972 mmol), and DCC (1.2441 g, 6.030 mmol) in dry CH$_2$Cl$_2$ (31 mL). The procedure and reaction conditions are similar to those employed for the preparation of 5. After 17 h, the reaction was worked-up similar to that of 5, and purification by flash-column chromatography with CH$_2$Cl$_2$:2% NH$_3$:3% MeOH yielded 0.3 g (72%) of the protected intermediate. After removal of the Boc group by treatment with 2N HCl (3 mL), AcOH (3 mL), and 3 drops of anisole at 25° C. for 105 min, the benzyl ester protected intermediate was worked up as the Boc-deprotection of 6 and purified by flash-column chromatography with CH$_2$Cl$_2$:2% NH$_3$:5% MeOH. Cleavage of the benzyl ester by hydrogenation at 39 psi with 25 mg of 10% Pd/C in MeOH (8 mL) for 1 h, followed by the work-up analogous to the benzyl ester-deprotection of 6 then yielded 7.2HCl (0.0714 g, 20.5%): mp 185° C. (decomposes); [α]$_D^{25°\ C.}$+147° (c=0.10, MeOH); $^1$H NMR (DMSO-d$_6$) δ 1.937 (br s, 4H, —CH$_2$CH$_2$—), δ 2.795 (s, 3H, NCH$_3$), δ 2.967–4.170 (complex, 11H, 5 —CH$_2$— and 1 —CH—), δ 6.06 (m, 1H, —CH—), δ 6.965–7.611 (complex, 7H, aromatic), δ 8.4 (br s, exchangeable proton), δ 10.5 (s, exchangeable proton), δ 10.9 (br s, exchangeable, proton). MS (FAB) m/z 521.2. Anal. (C$_{25}$H$_{30}$N$_4$O$_4$Cl$_2$.2HCl) calcd.: C 50.52, H 5.43, N 9.43, Cl 23.86; found: C 50.33, H 5.50, N 9.35, Cl 23.67.

Example XIV

2-(3,4-Dichlorophenyl)-N-methyl-N-{[1S]-1-[N-(R-glutamic acid-α-amido)-3-aminophenyl]-2-[1-pyrrolidinyl]ethyl}acetamide (8)

To a mixture of 15 (0.1582 g, 0.389 mmol), N-t-Boc-D-glutamic acid-γ-t-butyl ester (0.2361 g, 0.778 mmol), and HOBT (0.1073 g, 0.794 mmol) in dry CH$_2$Cl$_2$ (4 mL) was added DCC (0.1657 g, 0.803 mmol) and dry CH$_2$Cl$_2$ (2 mL) with stirring in ice-H$_2$O bath under N$_2$, and then the mixture was stirred at 25° C. After 24 h, the reaction mixture was worked up as was done in the preparation of 5, and purification by flash-column chromatography eluting with CH$_2$Cl$_2$:2% NH$_3$:2% MeOH yielded 0.1906 g (71%) of the di-protected intermediate. After deprotection in 3N HCl (8 mL) and AcOH (8 mL) at 25° C. overnight, the mixture was evaporated to yield a clear film which formed a white solid after evaporation from iPrOH to yield 8.2HCl (0.1232 g, 52%): mp 173° C. (decomposes); $[\alpha]_D^{25°\ C.}$ +91.5° (c=0.26, MeOH); $^1$H NMR (DMSO-d$_6$) δ 1.937–1.953 (br s, 4H, —CH$_2$CH$_2$—), 2.04 (m, 2H, —CH$_2$—), 2.37 (m, 2H, —CH$_2$—), 2.81 (s, 3H, —NCH$_3$), 3.07–4.12 (complex, 9H, 4 —CH$_2$—, 1 —CH—), 6.08 (m, 1H, —CH—), 7.03 (d, 1H, J=8 Hz, C$_6$H$_4$—), 7.29 (d, 1H, J=8 Hz, C$_6$H$_3$—), 7.35 (t, 1H, J=8 Hz, C$_6$H$_4$—), 7.49–7.55 (m, 2H, C$_6$H$_3$—), 7.56 (s, 1H, C$_6$H$_4$—), 7.65 (d, 1H, J=9 Hz, C$_6$H$_4$—). MS (FAB) m/z 535.2. Anal. (C$_{26}$H$_{32}$N$_4$O$_4$Cl$_2$.2HCl.0.1H$_2$O) calcd.: C 51.18, H 5.65, N 9.18; found: C 50.96, H 5.70, N 8.79.

Example XV 2-(3,4-Dichlorophenyl)-N-methyl-N-{[1S]-1-[N-(S-glutamic acid-α-amido)-3-aminophenyl]-2-[1-pyrrolidinyl]ethyl}acetamide (9)

Compound 9 was prepared from 15 (0.1468 g, 0.361 mmol), N-t-Boc-L-glutamic acid-γ-t-butyl ester (0.2192 g, 0.723 mmol), HOBT (0.0999 g, 0.739 mmol), and DCC (0.1548 g, 0.750 mmol) in dry CH$_2$Cl$_2$ (8 mL). The procedure and reaction conditions are similar to those employed for the preparation of 8. After 17 h, the reaction was worked-up similar to that of 8, and flash-column chromatography eluting with CH$_2$Cl$_2$:2% NH$_3$:2% MeOH yielded 0.2116 g (85%) of the di-protected intermediate. Complete deprotection was achieved in 3N HCl (8 mL) and AcOH (8 mL) at 25° C. overnight, but TLC indicated the presence of possibly the methyl ester after work-up. The methyl ester was hydrolyzed by stirring in 4N HCl at 35° C. for 1 h before the mixture was evaporated to give an oil which solidified after addition and evaporation of iPrOH to yield 9.2HCl (0.1577 g, 72%): mp 166° C. (decomposes); $[\alpha]_D^{25°\ C.}$+120° (c=0.25, MeOH); $^1$H NMR (DMSO-d$_6$) δ 1.94 (br s, 4H, —CH$_2$CH$_2$—), 2.03 (m, 2H, —CH$_2$—), 2.36 (m, 2H, —CH$_2$—), 2.80 (s, 3H, —NCH$_3$), 3.07–4.12 (complex, 9H, 4 —CH$_2$—, 1 —CH—), 6.08 (m, 1H, —CH—), 7.02 (d, 1H, J=8 Hz, C$_6$H$_4$—), 7.29 (d, 1H, J=9 Hz, C$_6$H$_3$—), 7.35 (t, 1H, J=8 Hz, C$_6$H$_4$—), 7.48–7.54 (m, 2H, C$_6$H$_3$—), 7.56 (s, 1H, C$_6$H$_4$—), 7.68 (d, 1H, J=8 Hz, C$_6$H$_4$—). MS (FAB) m/z 535.2. Anal. (C$_{26}$H$_{32}$N$_4$O$_4$Cl$_2$.2HCl.0.25iPrOH.1H$_2$O) calcd.: C 50.09, H 5.97, N 8.74; found: C 49.89, H 6.01, N 8.37.

Example XVI 2-(3,4-Dichlorophenyl)-N-methyl-N-([1S]-1-[N-(R-glutamic acid-γ-amido)-3-aminophenyl]-2-[1-pyrrolidinyl]ethyl}acetamide (10)

Compound 10 was prepared from 15 (0.2499 g, 0.615 mmol), N-Cbz-D-glutamic acid-α-benzyl ester (0.4567 g, 1.230 mmol), HOBT (0.1694 g, 1.254 mmol), and DCC (0.2614 g, 1.267 mmol) in dry CH$_2$Cl$_2$ (12 mL). The procedure and reaction conditions are similar to those employed for the preparation of 8. After 23 h, the reaction was worked-up similar to that of 8, and flash-column chromatographed eluting with CH$_2$Cl$_2$:2% NH$_3$:3% MeOH. One more flash-column eluting with CH$_2$Cl$_2$:2% NH$_3$:2% MeOH was required before 0.3326 g (68%) of the HCl salt of the di-protected intermediate was deprotected in MeOH (6 mL) by hydrogenation with 52 mg of 10% Pd/C at 25° C. under 40 psi. After removal of Pd/C and MeOH, the mixture was treated with 2N HCl (4 mL) and evaporated to give an oil which solidified after addition and evaporation of iPrOH to yield 10.2HCl (0.2081 g, 56%): mp 150° C. (decomposes); $[\alpha]_D^{25°\ C.}$+100° (c=0.24, MeOH); $^1$H NMR (DMSO-d$_6$) δ 1.93 (br s, 4H, —CH$_2$CH$_2$—), 2.07 (m, 2H, —CH$_2$—), 2.56 (m, 2H, —CH$_2$—), 2.79 (s, 3H, —NCH$_3$), 3.0–4.13 (complex, 9H, 4 —CH$_2$—, 1 —CH—), 6.05 (m, 1H, —CH—), 6.94 (d, 1H, J=7 Hz, C$_6$H$_4$—), 7.25–7.31 (m, 2H, aromatic), 7.47–7.53 (m, 2H, C$_6$H$_3$—), 7.56 (s, 1H, C$_6$H$_4$—), 7.61 (d, 1H, J=8 Hz, C$_6$H$_4$—). MS (FAB) m/z 535.2. Anal. (C$_{26}$H$_{32}$N$_4$O$_4$Cl$_{2.2}$HCl.0.25iPrOH) calcd.: C 51.54, H 5.82, N 8.99; found: C 51.90, H 6.06, N 8.64.

Example XVII 2-(3,4-Dichlorophenyl)-N-methyl-N-{[1S]-1-[N-(S-glutamic acid-γ-amido)-3-aminophenyl]-2-[1-pyrrolidinyl]ethyl}acetamide (11)

Compound 11 was prepared from 15 (0.1915 g, 0.471 mmol), N-t-Boc-L-glutamic acid-α-t-butyl ester (0.2144 g, 0.707 mmol), HOBT (0.0975 g, 0.722 mmol), and DCC (0.1533 g, 0.743 mmol) in dry CH$_2$Cl$_2$ (18 mL). The procedure and reaction conditions are similar to those employed for the preparation of 5. The reaction was incomplete after 22 h, and N-t-Boc-L-glutamic acid-α-t-butyl ester (0.1431 g, 0.472 mmol), HOBT (0.0654 g, 0.484 mmol), and DCC (0.1008 g, 0.488 mmol) in dry CH$_2$Cl$_2$ (2 mL) were added with ice cooling, followed by stirring at 25° C. for 24 h before the reaction was worked-up as in the preparation of 5. Flash-column chromatography eluting with CH$_2$Cl$_2$:5% MeOH yielded 0.2531 g (78%) of the di-protected intermediate, which was deprotected in TFA (trifluoroacetic acid) (10 mL) and 4 dr of anisole at 25° C. overnight. After evaporation of TFA, some Et$_2$O.HCl was added and then evaporated to yield an oil which formed a white solid after evaporation from iPrOH. Elemental analysis indicated the 0.2081 g of 11 to be a mixture of HCl and TFA salts: mp 136° C. (decomposes); $[\alpha]_D^{25°\ C.}$+89° (c=0.19, MeOH); $^1$H NMR (DMSO-d$_6$) δ 1.94 (br s, 4H, —CH$_2$CH$_2$—), 2.05 (m, 2H, —CH$_2$—), 2.3–2.6 (m, 2H, —CH$_2$—), 2.77 (s, 3H, —NCH$_3$), 3.0–4.08 (complex, 9H, 4 —CH$_2$—, 1 —CH—), 6.05 (m, 1H, —CH—), 6.94 (d, 1H, J=8 Hz, C$_6$H$_4$—), 7.26–7.31 (m, 2H, aromatic), 7.47–7.51 (m, 2H, C$_6$H$_3$—), 7.53 (s, 1H, C$_6$H$_4$—), 7.58 (d, 1H, J=8 Hz, C$_6$H$_4$—). MS (FAB) m/z 535.2. Anal. (C$_{26}$H$_{32}$N$_4$O$_4$Cl$_2$.0.75HCl.1.25TFA.0.5iPrOH) calcd.: C 49.00, H 5.21, N 7.62; found: C 49.00, H 5.47, N 7.64.

Example XVIII 2-(3,4-Dichlorophenyl)-N-methyl-N-{[1S]-1-[N-(N-CBZ-glycinamido)-3-aminophenyl]-2-[1-pyrrolidinyl]ethyl}acetamide (24)

To an ice-cold solution of N-Cbz-Gly (0.2449 g, 1.17 mmol) in dry CH$_2$Cl$_2$ under N$_2$ was added HOBT (0.1599 g, 1.18 mmol), followed by a CH$_2$Cl$_2$ solution of DCC (0.2467 g, 1.20 mmol). After 1 h at 0° C., a CH$_2$Cl$_2$ solution of 15 (0.3174 g, 0.781 mmol) was added, and the reaction mixture was stirred at 25° C. under N$_2$ for 4 days before it was filtered through celite. The residue after evaporation of the filtrate was dissolved in EtOAc, washed successively with saturated NaHCO$_3$ and water, and the organic fraction was dried (MgSO$_4$), filtered, and evaporated. Yield after flash-column chromatography with CHCl$_3$:2% NH$_3$:5% MeOH and crystallization of 24.HCl yielded 0.3178 g (68%) in the first crop: mp (24.HCl) softens at 125°–130° C., melts at 220° C.; $[\alpha]_D^{25\ C.}$+113.6° (c=0.28, 24.HCl, MeOH); $^1$H NMR (24.HCl, DMSO-d$_6$) δ 1.90–1.95 (m, 4H, —CH$_2$CH$_2$—), δ 2.76 (s, 3H, NCH$_3$), δ 3–4.1 (complex, 10H, 5 CH$_2$), δ 5.01 (s, 2H, ArCH$_2$O), δ 6.07 (m, 1H, CH), δ 6.94 (m, 1H, amide H), δ 7.25–7.56 (complex, 12H, aromatic H), δ 10.1 (s, 1H, amide H). MS (FAB) m/z 597.2. Anal. ($C_{31}H_{34}N_4O_4Cl_2 \cdot HCl$) calcd.: C 58.73, H 5.56, N 8.84, Cl 16.78; found: C 58.82, H 5.66, N 8.84, Cl 16.71.

EXAMPLE XIX

Pharmacological Activity

Target compounds were tested on the electrically stimulated guinea pig longitudinal ileal muscle (GPI) preparations (Rang, *Br. J. Pharmacol.* 22:356–365 (1964)) and mouse vas deferens (MVD) preparations (Henderson et al., *Br. J Pharmacol.* 46:764–766 (1972)) as described previously (Portoghese et al., *Life Sci.* 36:801–805 (1985)). The antagonist potency of the κ antagonist, norbinaltorphimine (norBNI), was expressed as $K_e$ values which were calculated from the equation $K_e$=[antagonist]/($IC_{50}$ratio-1), where the $IC_{50}$ ratio represents the $IC_{50}$ of the agonist in the presence of the antagonist divided by the control $IC_{50}$ of the agonist in the same preparation.

As shown in Tables 1 and 2, all ligands behaved as full agonists in both GPI and MVD. Furthermore, (±)-16, in spite of being racemic, retained potencies comparable to the more potent enantiomer 15 in the GPI. In addition, the smooth muscle data confirmed that the opioid activity resides predominantly with the S isomer as reported previously. In order to demonstrate that the agonist activities of (±)-S-33 in the GPI were mediated through interaction with κ opioid receptors, the GPI preparation was incubated with the κ antagonist, norBNI (20 nM), for 15 min before the agonists were tested. The $K_e$ values against (+)-33 (0.05 nM) strongly suggest that κ receptors are involved.

TABLE 1

Agonist Potencies of Parent Compounds in Smooth Muscle Preparations

| compd | isomer | $R^b$ | $IC_{50}$ (nM) ± $SEM^a$ GPI | MVD |
|---|---|---|---|---|
| (+)-3 | S | H | 0.27 ± 0.09 | 2.50 ± 1.65 |
| (−)-3 | R | H | 198 ± 43 | 87.0 ± 10.7 |
| 15 | S | 3-$NH_2$ | 0.17 ± 0.08 | 0.12 ± 0.01 |
| (±)-16 | R,S | 4-$NH_2$ | 0.65 ± 0.20 | 4.45 ± 1.39 |
| 14 | S | 3-$NO_2$ | 16.2 ± 6.7 | 2.49 ± 0.80 |
| 23 | R,S | 4-$NO_2$ | 100 ± 36 | 197 ± 61 |

[a] Values are arithmetic means of at least three experiments.
[b] R substitutions of Formula II.

Table 2 summarizes the agonist potencies of 5–7 and 10 on smooth muscle preparations.

TABLE 2

Agonist Potencies of Amino-Acid Conjugates in Smooth Muscle Prepns.

| Compound | GPI - $IC_{50}$ (nM) | MVD - $IC_{50}$ (nM) |
|---|---|---|
| 5 | 0.84 ± 0.30 | 2.49 ± 0.64 |
| 6 | 4.59 ± 1.11 | 4.06 ± 1.46 |
| 7 | 0.55 ± 0.16 | 6.36 ± 1.44 |
| 10 | 0.39 ± 0.10 | not tested |

Values are arithmetic means of at least three experiments.

EXAMPLE XX

Binding

The opioid receptor binding affinities and selectivities of selected compounds were determined by competition with radioligands in guinea pig brain membranes employing a modification of the method of Werling et al. (*J. Pharmacol. Exp. Ther.* 233:722–728 (1985)). Binding to κ receptors was evaluated with 1 nM [$^3$H]-(5α, 7α, 8β)-(−)-N-methyl-N-1-pyrrolidinyl-1-oxaspiro[4.5]dec-8-yl-benzeneacetamide (U69,593) (Lahti et al., *Eur. J. Pharmacol.* 109:281–284 (1985)), to μ receptors with 2 nM [$^3$H][D-Ala$^2$, MePhe$^4$, gly-ol$^6$]-enkephalin (DAMGO) (Handa et al., *Eur. J. Pharmacol.* 70:531–540 (1981)), to $\delta_1$ receptors with 5 nM [$^3$H][D-Pen$^2$, D-Pen$^5$]enkephalin (DPDPE) (Mosberg et al., *Proc. Natl. Acad. Sci. USA* 80:5871–5874 (1983)), and to $\delta_2$ receptors with 2 nM [$^3$H]Tyr-D-Ser-Gly-Phe-Leu-Thr (DSLET) (Gacel et al., *FEBS Lett.* 118:245–247 (1980)).

As shown on Table 3, derivatives (5, 6) retained high affinity and selectivity binding to the κ opioid receptor.

TABLE 3

Opioid Receptor Binding Selectivities in Guinea-Pig Brain

| | $K_i$ (nM) | | | selectivity | |
|---|---|---|---|---|---|
| cmpd | κ | μ | $\delta_2$ | μ/κ | $\delta_2$/κ |
| 5 | 0.20 | 449 | 1047 | 2,267 | 5,287 |
| 6 | 0.97 | 258 | 572 | 266 | 590 |

[a] Values are geometric means of three experiments.

EXAMPLE XXII

In Vivo Studies

The majority of target compounds were evaluated for in vivo activity using the mouse abdominal stretch assay (Hayashi et al., *Eur. J. Pharmacol.* 16:63–66 (1971)). In evaluating agonist selectivity, norBNI, naltrindole (NTI) (Portoghese et al., *J. Med. Chem.* 33:1714–1720 (1990)), and β-finaltrexamine (β-FNA) (Takemori et al., *Eur. J. Pharmacol.* 70:445–451 (1981)) were employed as κ-, δ-, and μ-selective antagonists, respectively. The determination of antagonist selectivity was carried out using U50,488, [D-Pen$^2$, D-Pen$^5$] Enkephalin (DPDPE), and morphine as κ-, δ-, and μ- selective agonists, respectively.

Amino-acid conjugates 5–7 were evaluated in vivo to determine their peripheral selectivity. As shown by the data on Table 4, when tested in the abdominal stretch assay, the derivatives 5–7 were considerably less potent than (+)-3, when administered by the i.v. route, whereas they were approximately equipotent with 3 by the i.c.v. route. The selectivity ratios of 5–7 were between 11- and 40-fold greater than parent compound 3.

TABLE 4

Antinociceptive Potencies of 55–57 in Mice.

| Compound | Assay | icv - $ED_{50}$ | iv - $ED_{50}$ | selectivity |
|---|---|---|---|---|
| 5 | writhing | 6.8 | 105 | 15.7 |
| 6 | writhing | 46 | 2015 | 43.6 |
| 7 | writhing | 11 | 628 | 56.5 |
| 3 | writhing | 12 | 17 | 1.4 |

$ED_{50}$ expressed in nmol/Kg - converted from units of nmol/mouse to nmol/Kg by employing the average weight of 25 g/mouse. Selectivity = iv/icv.

The antinociceptive effects of compounds 5 and 7 in the mouse abdominal stretch assay were also found to be κ-selective, as indicated by the fact that the κ-selective antagonist nor-BNI significantly increased the $ED_{50}$ values of 5 and 7, while the μ and δ antagonists, β-FNA and NTI, were ineffective in this regard (Table 5). Surprisingly, the $ED_{50}$ of 6 was not affected significantly by any of the three opioid receptor selective antagonists.

TABLE 5

Receptor Selectivity of 5–7 Antinociception in the Mouse Abdominal Stretch Assay.

| Compound | norBNI (κ)[a] | NTI (δ)[b] | β-FNA (μ)[c] |
|---|---|---|---|
| 5 | 5.00 (3.13–8.33) | 0.92 (0.56–1.49) | 2.86 (1.69–4.76) |
| 6 | 1.69 (0.83–2.94) | 0.55 (0.28–0.96) | 1.75 (0.88–3.23) |
| 7 | 7.14 (5.00–11.11) | 1.01 (0.66–1.56) | 2.56 (1.67–4.00) |

Expressed as $ED_{50}$ ratio - $ED_{50}$ of the agonist (sc) in the antagonist-treated mice divided by the control $ED_{50}$.
[a]12.25 μmol/kg sc, 2 h peak time.
[b]20.37 μmol/kg sc, 24 h peak time.
[c]44.44 μmol/kg sc, 30 min peak time.
Numbers in parentheses are 95% confidence levels.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of the formula (I):

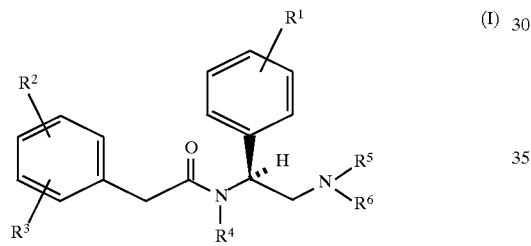

where $R^2$ is H or halo;
$R^3$ is halo; or
$R^2$ and $R^3$ are at adjacent carbon atoms, and together with the carbon atoms are a 5–7 membered aromatic or aliphatic ring fused with the phenyl ring;
$R^4$ is ($C_1$–$C_4$) alkyl;
$R^5$ and $R^6$ are independently selected from ($C_1$–$C_4$) alkyl, or together with N are a 5 membered aromatic or aliphatic ring, said ring being optionally substituted with hydroxy($C_1$–$C_4$)alkyl, OH, CHO or [($C_1$–$C_4$) alkyl] C=O group; $R^1$ is N($R^7$)C(O)—A(B)(C) wherein $R^7$ is H or ($C_1$–$C_4$)alkyl, A is ($C_1$–$C_5$)alkyl, B is amino and C is H, OH, $CH_3$, $SR^8$, phenyl, 4-hydroxyphenyl, indol-3-yl, $CO_2R^8$, $SO_3R^8$, $CO_2N(R^8)_2$, $N(R^8)_2$ or guanidino, wherein each $R^8$ is H, benzyl or ($C_1$–$C_4$)alkyl, or wherein A(B)(C) together are pyrrolidin-2-yl or 4-hydroxy-pyrrolidin-2-yl;
or a pharmaceutically acceptable salt thereof.

2. The compound of claim 1, wherein $R^1$ is —N($R^7$)C(O)CH($NH_2$)($CH_2$)$_{1-3}$$CO_2R^8$ or —N($R^7$)C(O)($CH_2$)$_{1-3}$CH($NH_2$)$CO_2R^8$, and $R^8$ is H or ($C_1$–$C_4$)alkyl.

3. A compound of claim 1 wherein $R^2$ and $R^3$ are halo.

4. A compound of claim 1 wherein $R^2$ and $R^3$ are Cl.

5. A compound of claim 2 wherein $R^2$ is at the 4-position and $R^3$ is at the 3-position of the phenyl ring.

6. A compound of claim 1 wherein $R^4$ is $CH_3$.

7. A compound of claim 1 wherein $R^5$ and $R^6$ together with N are pyrrolidinyl.

8. A compound of claim 6 where $R^5$ and $R^6$ together with N are pyrrolidinyl.

9. A compound of claim 7 where said pyrrolidinyl ring is substituted at the 3-position with $CH_2OH$, OH, $CH_3C(O)$ or CHO.

10. A compound of claim 6 wherein $R^7$ is H.

11. A compound of claim 6 wherein $R^1$ is at the 3- or 4-position of the phenyl ring.

12. A compound of claim 1 or 6 wherein $R^1$ is N(H)C(O)CH($NH_2$)$CH_2CO_2H$.

13. A compound of claim 1 or 6 wherein $R^1$ is N(H)C(O)CH($NH_2$)($CH_2$)$_2CO_2H$.

14. A compound of claim 1 or 6 wherein $R^1$ is N(H)C(O)$CH_2$CH($NH_2$)$CO_2H$.

15. A compound of claim 1 or 6 wherein $R^1$ is N(H)C(O)$CH_2CH_2$CH($NH_2$)$CO_2H$.

16. A compound according to claim 1 wherein $R^2$ and $R^3$ form a 5-membered ring.

17. A compound according to claim 1 wherein $R^2$ and $R^3$ are benzo.

18. A compound of the formula (II):

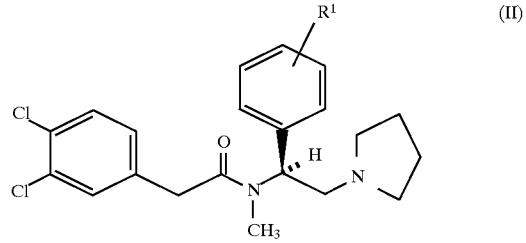

where R is N(H)C(O)CH($NH_2$)$CH_2CO_2H$, N(H)C(O)CH($NH_2$)($CH_2$)$_2CO_2H$, N(H)C(O)$CH_2$CH($NH_2$)$CO_2H$, N(H)C(O)$CH_2CH_2$CH($NH_2$)$CO_2H$, or a pharmaceutically acceptable salt thereof.

19. A compound of claim 18 wherein $R^1$ is:

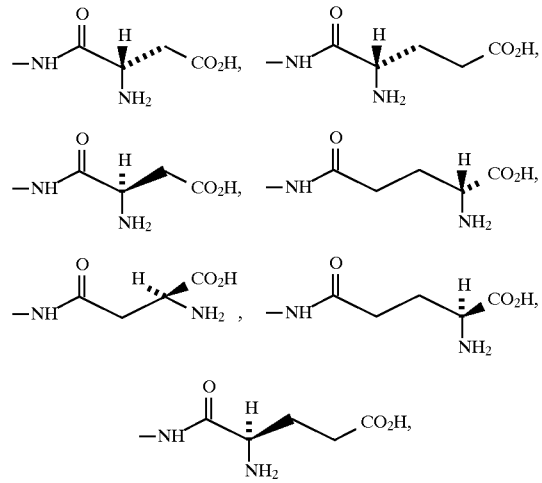

or a pharmaceutically acceptable salt thereof.

20. 2-(3,4-dichlorophenyl)-N-methyl-N-{[1S]-1-[N-(S-aspartic acid-α-amido)-3-aminophenyl]-2-[1-pyrrolidinyl] ethyl}acetamide.

21. 2-(3,4-dichlorophenyl)-N-methyl-N-{[1S]-1-[N-(R-aspartic acid-α-amido)-3-aminophenyl]-2-[1-pyrrolidinyl] ethyl}acetamide.

22. 2-(3,4-dichlorophenyl)-N-methyl-N-{[1S]-1-[N-(S-aspartic acid-β-amido)-3-aminophenyl]-2-[1-pyrrolidinyl] ethyl}acetamide.

23. 2-(3,4-dichlorophenyl)-N-methyl-N-{[1S]-1-[N-(R-glutamic acid-α-amido)-3-aminophenyl]-2-[1-pyrrolidinyl]ethyl}acetamide.

24. 2-(3,4-dichlorophenyl)-N-methyl-N-{[1S]-1-[N-(S-glutamic acid-α-amido)-3-aminophenyl]-2-[1-pyrrolidinyl]ethyl}acetamide.

25. 2-(3,4-dichlorophenyl)-N-methyl-N-{[1S]-1-[N-(R-glutamic acid-γ-amido)-3-aminophenyl]-2-[1-pyrrolidinyl]ethyl}acetamide.

26. 2-(3,4-dichlorophenyl)-N-methyl-N-{[1S]-1-[N-(S-glutamic acid-γ-amido)-3-aminophenyl]-2-[1-pyrrolidinyl]ethyl}acetamide.

27. A method of alleviating inflammatory pain comprising administering to a mammalian host in need of such treatment an effective amount of the compound of claims 1 or 18.

28. The method of claim 27 wherein said pain is caused by rheumatoid arthritis.

29. The method of claim 27 wherein said pain is caused by laparoscopic surgery.

30. A method of agonizing kappa-opioid receptors comprising contacting a mammalian tissue or mammalian cell, wherein said tissue or cell incorporates kappa-opioid receptors, with an amount of a compound according to claim 1 effective to bind to said kappa-opioid receptors.

31. The method according to claim 30 wherein said tissues or cells are peripherally located.

32. The method according to claim 30 wherein said tissue is gastrointestinal tissue.

33. A pharmaceutical composition comprising an effective anti-inflammatory amount of a compound of claim 1 or 18 in combination with a pharmaceutically acceptable carrier.

* * * * *